(12) United States Patent
Chen et al.

(10) Patent No.: US 7,947,949 B2
(45) Date of Patent: May 24, 2011

(54) SAMPLE PROCESSING SYSTEM AND SAMPLE PROCESSING METHOD FOR TRACE DETECTOR

(75) Inventors: Zhiqiang Chen, Beijing (CN); Yuanjing Li, Beijing (CN); Hua Peng, Beijing (CN); Wen He, Beijing (CN); Hui Li, Beijing (CN); Zhongxia Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 241 days.

(21) Appl. No.: 12/422,427

(22) Filed: Apr. 13, 2009

(65) Prior Publication Data

US 2009/0289183 A1    Nov. 26, 2009

(30) Foreign Application Priority Data

May 21, 2008   (CN) .............................. 200810112209

(51) Int. Cl.
*G01N 1/10* (2006.01)
*G01N 13/00* (2006.01)
*B01D 59/44* (2006.01)

(52) U.S. Cl. .......... 250/288; 250/281; 250/282; 73/863; 73/863.51; 506/6; 436/180

(58) Field of Classification Search ............... 250/288, 250/281, 282; 73/863, 863.51; 436/180; 506/6
See application file for complete search history.

(56) References Cited

U.S. PATENT DOCUMENTS

| | | | |
|---|---|---|---|
| 3,699,333 A | 10/1972 | Cohen et al. | 250/41.9 |
| 4,311,669 A | 1/1982 | Spangler | 422/98 |
| 4,551,624 A | 11/1985 | Spangler et al. | 250/287 |
| 4,777,363 A | 10/1988 | Eiceman et al. | 250/286 |
| 5,425,263 A | 6/1995 | Davies et al. | 73/28.05 |
| 5,476,794 A | 12/1995 | O'Brien et al. | 436/92 |
| 5,571,976 A | 11/1996 | Drolet | 73/864.71 |
| 5,859,375 A | 1/1999 | Danylewych-May et al. | 73/864.71 |

(Continued)

FOREIGN PATENT DOCUMENTS

DE   69210676 T2   2/1992

(Continued)

*Primary Examiner* — Nikita Wells
(74) *Attorney, Agent, or Firm* — Westman, Champlin & Kelly, P.A.

(57) ABSTRACT

A sample processing system and a sample processing method for a trace detector are disclosed. The system comprises a sampling substrate for collecting a substance or substances from the surface of an object to be tested by contacting the sampling substrate with the surface of the object, and a trace detector. The trace detector includes a sample feeding device provided with a sample feeding part. The substance collected by the sampling substrate can be transferred to a surface of the sample feeding part so that the substance transferred to the surface of the sample feeding part can be detected. With the configuration of some embodiments of the present invention, a sampling substrate made of chemical fiber is used to collect a sample from the surface of an object to be tested by contacting the sampling substrate with the surface of the object to be tested. The sample collected by the sampling substrate is mechanically transferred to a metal film or mesh of the sample feeding device of the trace detector. Then, the metal film or mesh of the sample feeding device is heated to vaporize the sample and to release the sample vapor into the trace detector. Therefore, the efficiency of sample collection and desorption processes can be improved. In addition, the direct heating of a sampling substrate can be avoided so as to decrease the interference of the sampling substrate with trace detection.

25 Claims, 5 Drawing Sheets

U.S. PATENT DOCUMENTS

| | | | |
|---|---|---|---|
| 6,265,226 B1 * | 7/2001 | Petro et al. | 506/12 |
| 6,436,292 B1 * | 8/2002 | Petro | 506/6 |
| 6,446,514 B1 * | 9/2002 | Danylewych-May et al. | 73/863.21 |
| 6,767,706 B2 * | 7/2004 | Quake et al. | 435/6 |
| 6,858,436 B2 * | 2/2005 | Zenhausern et al. | 436/164 |
| 6,870,155 B2 | 3/2005 | Krasnobaev et al. | 250/283 |
| 2005/0274205 A1 | 12/2005 | Sleeman et al. | 73/864 |
| 2005/0288616 A1 | 12/2005 | Bozenbury, Jr. et al. | 604/1 |
| 2006/0192098 A1 | 8/2006 | Danylewych-May | 250/281 |
| 2006/0249671 A1 | 11/2006 | Karpetsky | 250/288 |

FOREIGN PATENT DOCUMENTS

| | | |
|---|---|---|
| DE | 19502674 | 9/1996 |
| WO | WO 93/06476 | 4/1993 |

* cited by examiner (a)

(b)

(a)

(b)

SAMPLE PROCESSING SYSTEM AND SAMPLE PROCESSING METHOD FOR TRACE DETECTOR

The present application claims priority of Chinese patent application Serial No. 200810112209.1, filed May 21, 2008, the content of which is hereby incorporated by reference in its entirety.

BACKGROUND OF THE INVENTION

1. Field of the Invention

The present invention relates to a sample processing system and a sample processing method for a trace detector.

2. Description of the Related Art

A trace particle or liquid sample collected from a surface of an object under inspection can be tested by means of trace detection techniques. The trace detection techniques are particularly suitable for detection of harmful substances of trace level such as explosives, narcotics, chemical warfare agents, and biological warfare agents formed in the form of particles, aerosols, or liquid droplets.

The ion mobility spectrometry (IMS) is one of the trace detection techniques and is disclosed in patents such as U.S. Pat. Nos. 3,699,333 and 4,777,363. An example of the operation mode of an ion mobility spectrometer is shown in FIG. 1. Through forty years of research, rapid progress has been made in the equipment design, separation principle, and sampling techniques associated with IMS as disclosed in U.S. Pat. Nos. 4,311,669, 4,551,624, DE 19502674, and WO 9306476. Sampling techniques are mainly divided into non-contact sampling as disclosed in U.S. patent application Ser. No. 2006249671, and U.S. Pat. Nos. 6,870,155 and 5,425,263, and wipe sampling as disclosed in U.S. Pat. No. 5,859,375, and U.S. patent application Ser. Nos. 20060192098 and 20050288616.

FIGS. 1-5 are schematic diagrams showing conventional wipe sampling introduction method. As shown in FIGS. 2-5, a trace detector 10 comprises an ion mobility spectrometer 12 and a sample feeding device 14' for feeding a sample substrate 1 into the trace detector 10. A sampling substrate 1 collects a sample by contacting with a surface to be tested, and then is fed into the sample feeding device 14' and heated by a heater 3' therein to release (evaporate) the sample.

As shown in FIG. 4, for example, the ion mobility spectrometer 12 may comprise a sample gas inlet 16, an ion source Ni63 18, an ion gate 24, electrodes 22, a grid 26, and an ion detector 20.

FIGS. 2 and 3 are schematic diagrams showing conventional wipe sampling introduction method. As shown in FIGS. 2 and 3, the sample feeding device 14' comprises a part 2'. The part 2' is disposed on an side of the sample feeding device. The part 2' can be opened and closed, or drawn out of and pushed into the sample feeding device. The sample feeding device further comprises a heater 3' for evaporating a sample from a sample substrate 1. A sampling substrate 1 collects a sample by contacting with a surface to be tested, and then fed into the sample feeding device and heated by heater 3' therein to release (evaporate) the sample.

By using the prior art sample processing method, the sampling substrate is heated directly in order to evaporate the sample. Most types of sample substrates will release interference substances to disturb the detection. It has proved to very difficult to find a proper material which has both high collection efficiency by swipe sampling and desired high temperature resistance.

SUMMARY OF THE INVENTION

Thus, there is a need in the art for a sample processing system and a sample processing method for trace detectors to avoid heating a sampling material directly.

In an embodiment, the present invention provides a sample processing system comprising a sampling substrate for collecting a substance from a surface of an object to be tested by contacting the sampling substrate with the surface of the object, and a trace detector. The trace detector includes a sample feeding device provided with a sample feeding part. The substance collected by the sampling substrate can be transferred to a surface of the sample feeding part so that the substance transferred to the surface of the sample feeding part can be detected in the trace detector.

In some embodiments, the sampling substrate may be sheet-shaped and may be made of at least one of material such as Dacron™, fiber of high density polyethylene, Terylen, and nylon.

In some preferred embodiments, the sample feeding part may be sheet-shaped.

In some embodiments, the sample feeding part may be made of metal, for example a metal film or a metal mesh.

In some embodiments, the metal may be stainless steel. In some embodiments, the metal may be one of Ni, Cr, and Pt or one of alloys including at least one of Ni, Cr, and Pt.

In some embodiments, the metal film may have a thickness of about 0.01-0.10 mm. The metal net may comprise wires having a diameter of about 0.01-0.10 mm and may have a mesh size of 300-800.

In another embodiment, the present invention provides a sample processing method for a trace detector. The trace detector includes a sample feeding device provided with a sample feeding part. The sample processing method comprises the steps of providing a sampling substrate, collecting a substance from a surface of an object to be tested by contacting the sampling substrate with the surface of the object to be tested, and transferring the substance collected by the sampling substrate to a surface of the sample feeding part of the sample feeding device.

In some embodiments, the sampling processing method may further comprise the step of detecting the substance transferred to the surface of the sample feeding part.

In a further embodiment, the present invention provides a trace detector. The trace detector includes a sample feeding device provided with a sample feeding part. A substance collected by a sampling substrate can be transferred to a surface of the sample feeding part so that the substance transferred to the surface of the sample feeding part can be detected.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
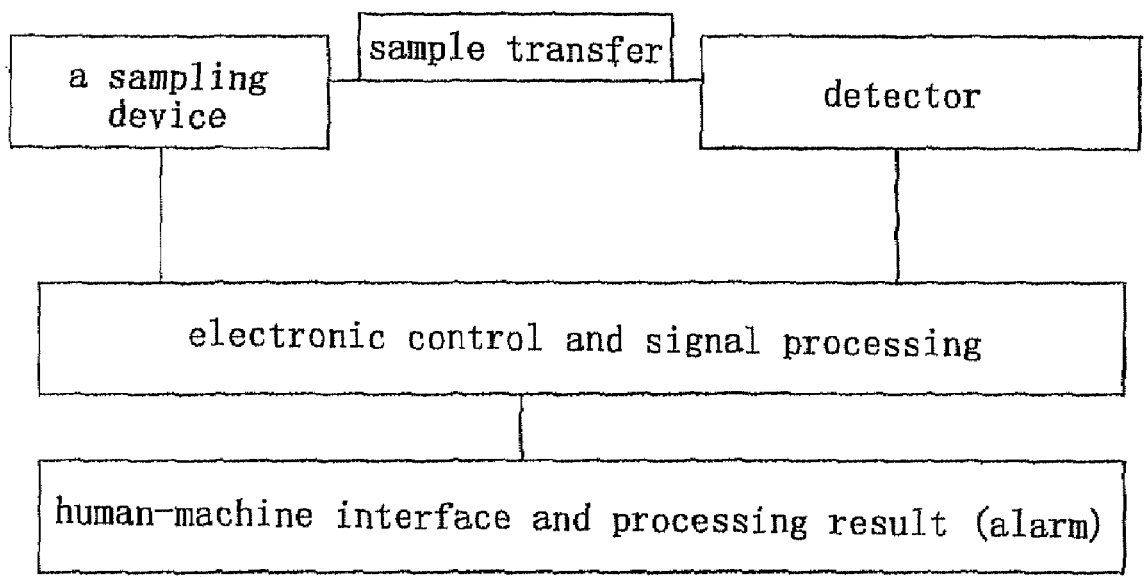
FIG. 1 is a schematic diagram showing an example of the operation mode of an ion mobility spectrometer.

Reference will now be made in detail to the present embodiments of the present invention, examples of which are illustrated in the accompanying drawings, wherein like reference numerals refer to the like elements throughout. The embodiments are described below in order to explain the present invention by referring to the figures. However, the present application is not limited to the embodiments.

Referring to FIGS. 6-9, a sample processing system according to an embodiment of the present invention comprises a sampling substrate 1 for collecting a substance from a surface of an object to be tested by contacting the sampling substrate with the surface of the object, and a trace detector such as an ion mobility spectrometer. The trace detector includes a sample feeding device provided with a metal film or mesh 4 as an example of a sample feeding part. The substance collected by the sampling substrate can be transferred to a surface of the metal film or mesh 4 so that the substance transferred to the surface of the metal film or mesh 4 can be detected. For example, the substance transferred to the surface of the metal film or mesh 4 can be fed into the trace detector for detection.

The metal film or mesh 4 may be a separate metal film or mesh disposed in the sample feeding device, or a metal layer formed on other components of the sample feeding device. Alternatively, the metal film or mesh 4 may be disposed on a heater 3. The heater 3 is used to heat the metal film or mesh 4 to release the substance, which is transferred to the metal film or mesh 4 from the sampling substrate 1, from the metal film or net 4. In addition, the metal film or mesh 4 can be replaced with a part made of other materials so long as the part is compatible with processes performed by the heater. Furthermore, the metal film or mesh 4 may be disposed at any appropriate position in the sample feeding device so long as the substance transferred to the metal film or mesh 4 can be detected in a manner similar to the conventional manner in which a substance collected by a sampling substrate 1 is detected by directly heating the sampling substrate 1 in a trace detector in the prior art. For example, in the sample feeding device, the metal film or mesh 4, a metal layer or a layer of other appropriate material may be disposed at a position where a sampling substrate 1 is generally placed in a prior art sample feeding device. The metal film or mesh 4, or another part substituting for the metal film or mesh 4 may have a sheet-like shape or any other appropriate shape.

In an embodiment, a sampling substrate 1 made of chemical fiber is used to collect a sample from a surface of an object to be tested by contacting the sampling substrate 1 with the surface of the object to be tested. The sample collected by the sampling substrate 1 is transferred to the metal film or mesh 4 of the sample feeding device of the trace detector in a mechanical manner, for example, by contacting the sampling substrate 1 with the metal film or mesh 4 by means of a hand operation. The metal film or mesh 4 is a part of the sample feeding device of the trace detector.

Figure 2:
FIG. 2 is a schematic diagram showing a conventional sample feeding device into which a sample is fed to be heated by opening a part of the sample feeding device.
Figure 3:
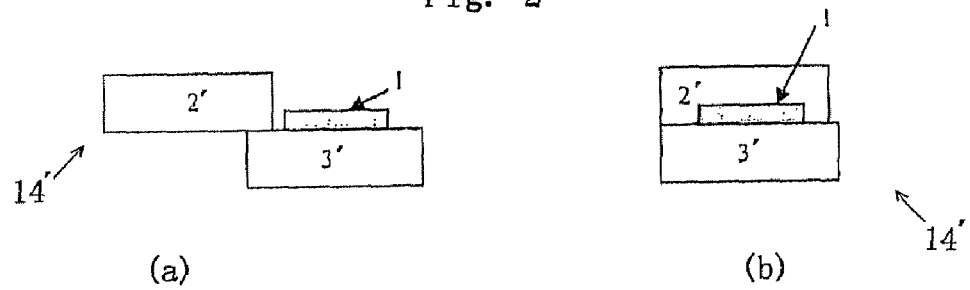
FIG. 3 is a schematic diagram showing another conventional sample feeding device into which a sample is fed to be heated by drawing out a part of the sample feeding device.
Figure 4:
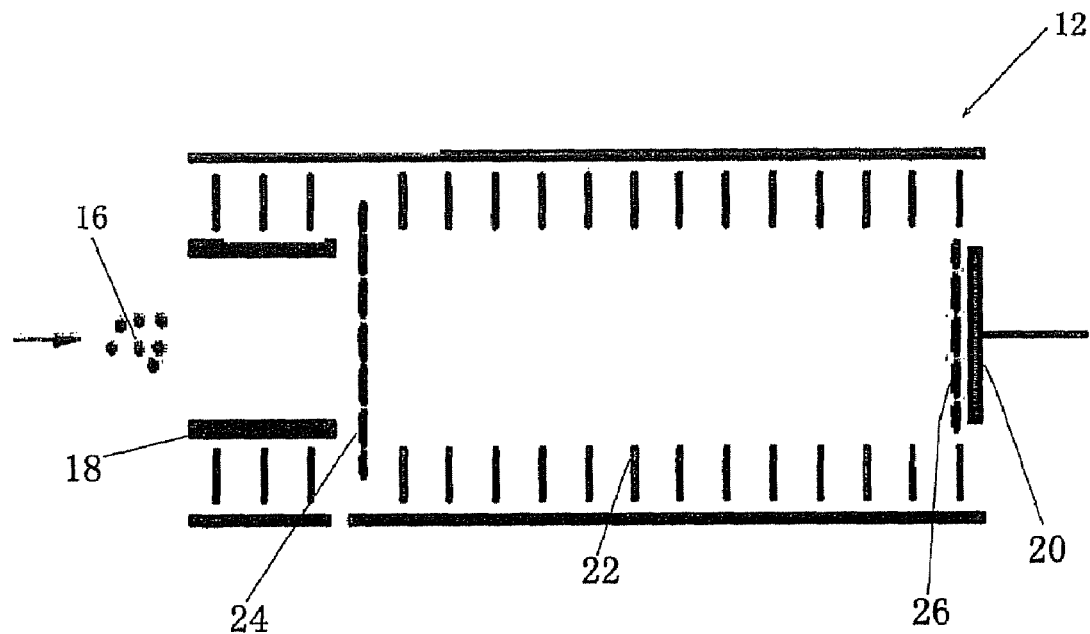
FIG. 4 is a schematic diagram showing an example of an ion mobility spectrometer.
Figure 5:
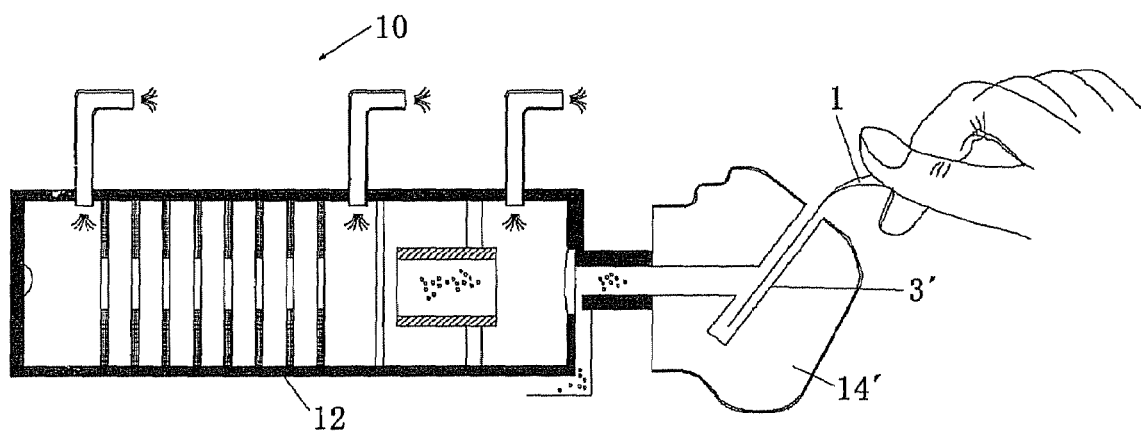
FIG. 5 is a diagram showing a part of a trace detector with a conventional wipe sampling introduction method.
Figure 6:
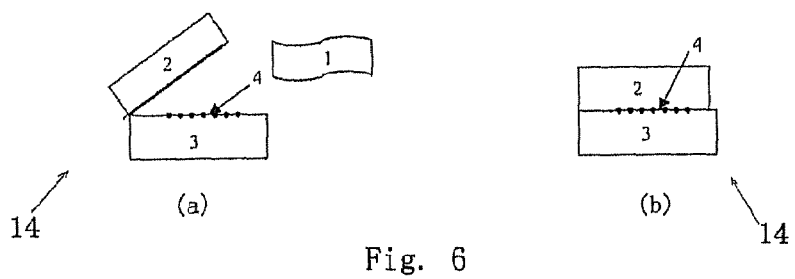
FIG. 6 is a schematic diagram showing a sample feeding device with a sample feeding part, in which a sample is transferred to a surface of the sample feeding part by opening a part of the sample feeding device, according to an embodiment of the present invention.
Figure 7:
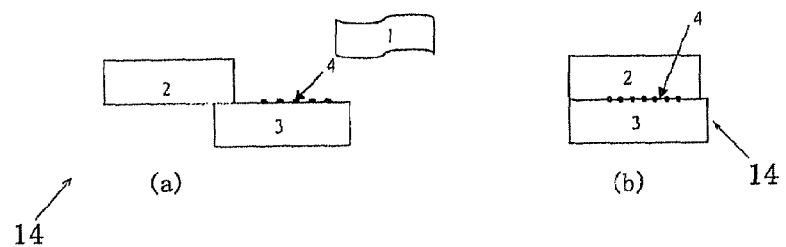
FIG. 7 is a schematic diagram showing a sample feeding device with a sample feeding part, in which a sample is transferred to a surface of the sample feeding part by drawing out a part of the sample feeding device, according to another embodiment of the present invention.
Figure 8:
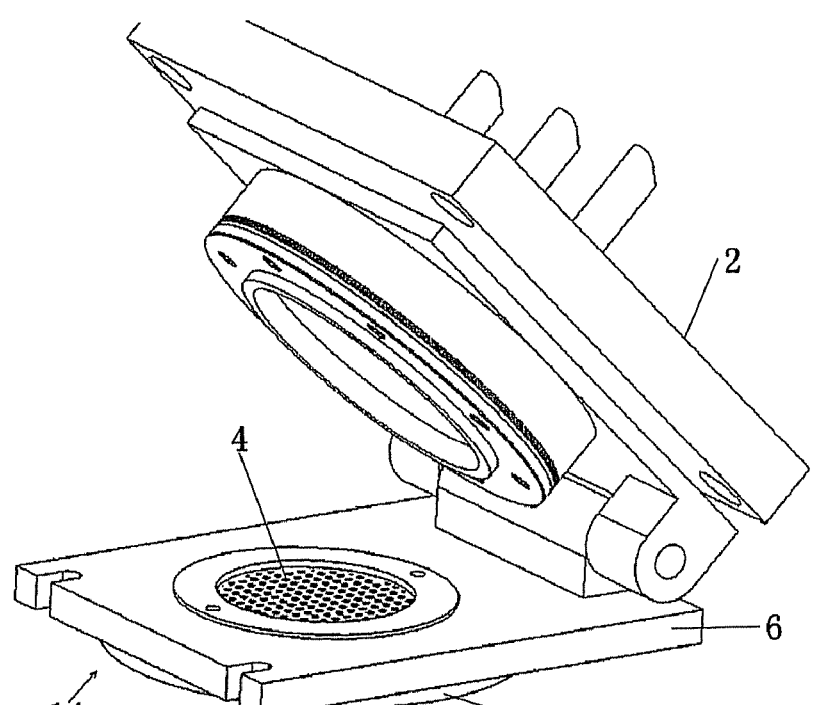
FIG. 8 is a schematic diagram of a sample feeding device with a sample feeding part, in which a sample is transferred to a surface of the sample feeding part by opening a part of the sample feeding device, according to an embodiment of the present invention.
Figure 8:
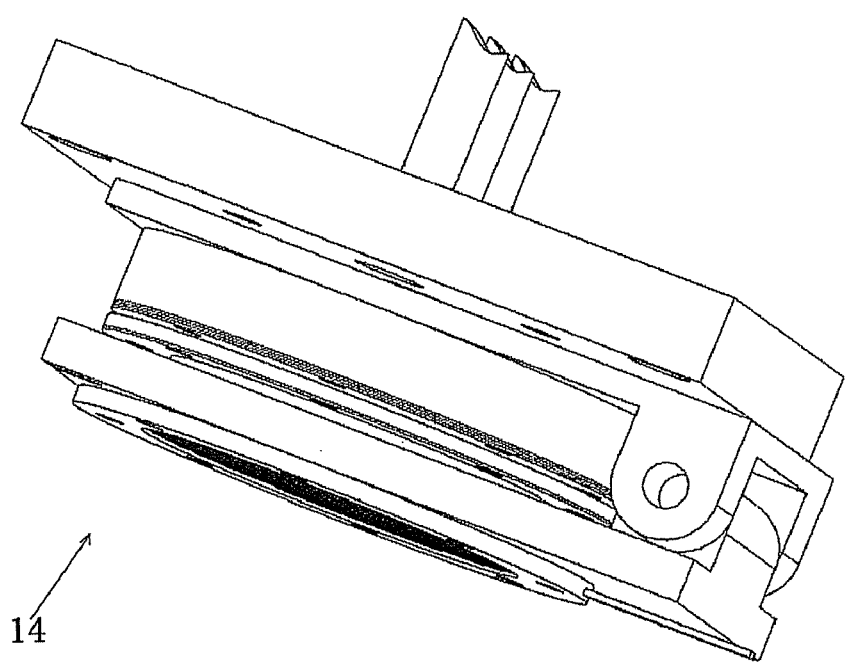
Figure 9:
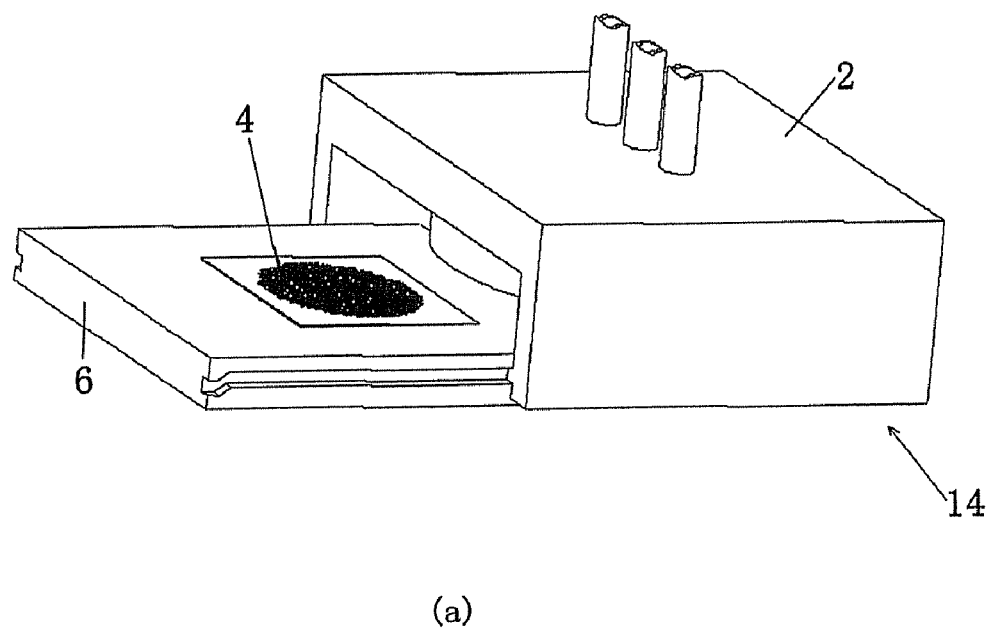
FIG. 9 is a schematic diagram of a sample feeding device with a sample feeding part, in which a sample is transferred to a surface of the sample feeding part by drawing out a part of the sample feeding device, according to another embodiment of the present invention.
Figure 9:
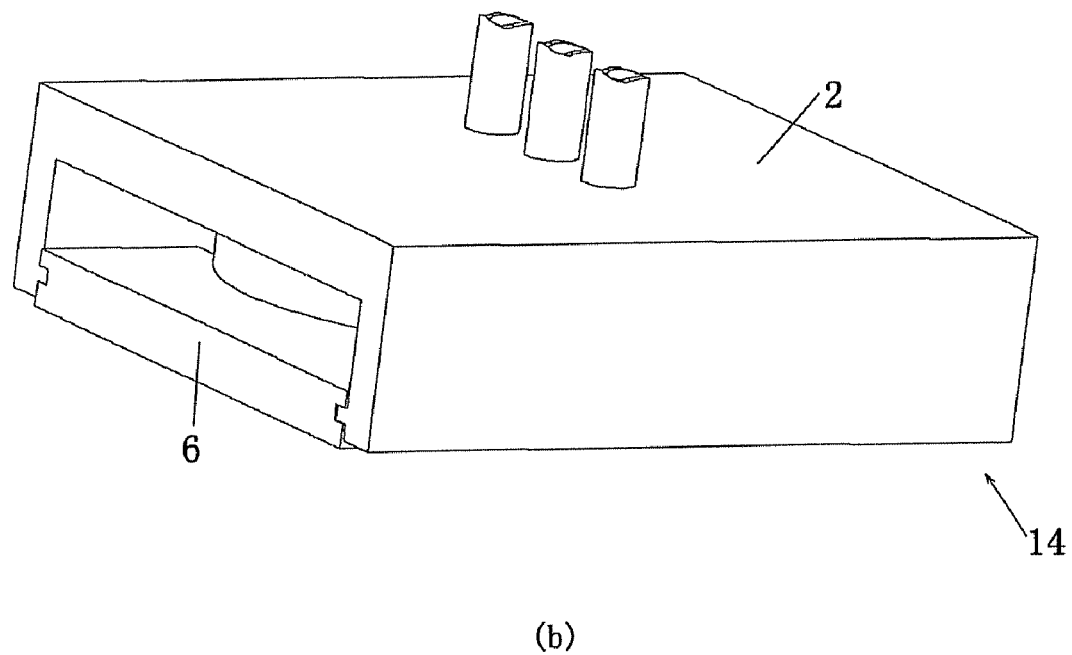

In an embodiment, the sample feeding device 14 may be configured as a part A 2 and a part B 6 as shown in FIGS. 6-9. The part A 2 of the sample feeding device can be opened as shown in FIGS. 6 and 8 or the part B 6 can be drawn out as shown in FIGS. 7 and 9. The part B 6 is used for feeding a sample into the sample feeding device 14. When the part A 2 is opened or the part B 6 is drawn out, the metal film or mesh 4 is exposed. Then, a sample collected by a sampling substrate 1 is transferred to the metal film or mesh 4. After that, the part A 2 or the part B 6 is returned and the substance transferred to the metal film or mesh 4 is released by heating the metal film or mesh 4 by means of a heater 3 disposed on a lower side of the part B 6. Since the metal film or mesh 4 is mechanically constructed together with the heater 3 as in FIGS. 8-9, it facilitates sample desorption more effectively than the sampling substrate 1 in the sample feeding device as in FIGS. 2-3 and 5. In addition, once a suspicious sample is found, the sampling substrate 1 corresponding to the suspicious sample can be sealed up for keeping so that the suspicious sample can be further analyzed and relevant evidence can be obtained.

In some embodiments, a sampling substrate 1 is made of chemical fiber. The chemical fiber has absorption and transfer properties suitable for trace analytes such as explosives, narcotics, chemical warfare agents and biological warfare agents. For example, materials of the sampling substrate 1 may comprise Dacron™, high density polyethylene fiber, Terylen, and nylon. The sampling substrate 1 may be sheet-shaped. In some embodiments, the sampling substrate 1 may have any appropriate shape, or any shape known to the art.

The metal used for the sample feeding part such as the metal film or net 4 may be any appropriate metal material such as stainless steel, so long as the metal material is compatible with the processes performed by the heater 3 and facilitates thermal desorption of substances from the sample feeding part such as the metal film or mesh 4 made of the metal material.

In a preferred embodiment, the metal for the sample feeding part such as the metal film or mesh 4 has low heat capacity and high transfer efficiency for particular analytes. The sample feeding part such as the metal film or mesh 4 may be cleaned quickly by high temperature heating.

In another embodiment, the metal may be one of Ni, Cr, and Pt or one of alloys of at least one of Ni, Cr, and Pt.

In some embodiments, the metal film may have a thickness of about 0.01-0.10 mm. The metal mesh may comprise wires having a diameter of about 0.01-0.10 mm and may have a mesh size of 300-800.

During operation of the sample feeding device, the metal film or mesh 4 is compatible with processes performed by the heater 3. The metal film or mesh 4 can resist a high temperature, and will not release a substance interfering with the detection. For example, when heated, the sample feeding part will not produce any gas interfering with the test result of the trace detector.

A sample processing method for a trace detector according to an embodiment of the present invention is now described. The sample processing method comprises the steps of providing a sampling substrate 1, collecting a substance from a surface of an object to be tested by contacting the sampling substrate 1 with the surface of the object to be tested, and transferring the substance collected by the sampling substrate 1 to a surface of a metal film or mesh 4 as a sample feeding part of a sample feeding device. The method may further comprise the steps of heating the metal film or mesh 4 to vaporize the substance transferred to the metal film or mesh 4 as a sample feeding part and release the substance into the trace detector for detection.

A trace detector according to an embodiment of the present invention is now described. The trace detector includes a sample feeding device provided with a sample feeding part. A substance collected by a sampling substrate 1 can be transferred to a surface of the sample feeding part so that the substance transferred to the surface of the sample feeding part can be detected.

In an embodiment, the sample feeding part may be disposed in the sample feeding device.

In some embodiments, the sample feeding device may comprise any appropriate sample feeding device known to the art, and the trace detector may be any appropriate trace detector known to the art.

With the configuration of some embodiments of the present invention, direct heating of a sampling substrate can be avoided so as to decrease the interference of the sampling substrate with the detection. In addition, since it is not necessary to heat the sampling substrate for degas treatment, the efficiency and speed of sampling substrate preparation are increased. Furthermore, the material of the sampling substrate can be selected from a broader range including those with good sampling performance and low cost. In addition, with the configuration of some embodiments of the present invention, an outstanding feature of the method relies on its capability to store the suspicious sample after detection and use it for a further test.

With the configuration of some embodiments of the present invention, a sampling substrate made of chemical fiber is used to collect a sample from a surface of an object to be tested by contacting the sampling substrate with the surface of the object to be tested. The sample collected by the sampling substrate is mechanically transferred to a sample feeding part such as a metal film or mesh of the sample feeding device of the trace detector. Then, the sample feeding part such as a metal film or mesh of the sample feeding device is heated to vaporize the sample and to release the sample vapor into the trace detector. Therefore, the efficiency of sample collection and desorption can be improved.

Although a few embodiments of the present invention have been shown and described, it would be appreciated by those skilled in the art that changes may be made in these embodiments without departing from the principles and spirit of the invention, the scope of which is defined in the claims and their equivalents. For example, some of the embodiments described above can be combined to form other embodiments unless the combination is not feasible.

What is claimed is:

1. A sample processing system, comprising:
    a sampling substrate for collecting a substance from a surface of an object to be tested by contacting the sampling substrate with the surface of the object, and
    a trace detector, wherein the trace detector includes a sample feeding device provided with a sample feeding part, and wherein the substance collected by the sampling substrate can be transferred to a surface of the sample feeding part so that the substance transferred to the surface of the sample feeding part can be detected.

2. The sample processing system according to claim 1, wherein the sampling substrate is a sheet-shaped substrate and is made of at least one of Dacron™, high density polyethylene fiber, terylen, and nylon.

3. The sample processing system according to claim 1, wherein the sample feeding part is a sheet-shaped substrate.

4. The sample processing system according to claim 3, wherein the sample feeding part is made of metal.

5. The sample processing system according to claim 3, wherein the sample feeding part is a film of metal.

6. The sample processing system according to claim 3, wherein the sample feeding part is a mesh of metal.

7. The sample processing system according to claim 5, wherein the metal comprises stainless steel.

8. The sample processing system according to claim 6, wherein the metal comprises stainless steel.

9. The sample processing system according to claim 5, wherein the metal comprises one of Ni, Cr, and Pt or one of alloys including at least one of Ni, Cr, and Pt.

10. The sample processing system according to claim 6, wherein the metal comprises one of Ni, Cr, and Pt or one of alloys including at least one of Ni, Cr, and Pt.

11. The sample processing system according to claim 5, wherein the film of metal has a thickness of about 0.01-0.10 mm.

12. The sample processing system according to claim 6, wherein the mesh of metal comprises wires having a diameter of about 0.01-0.10 mm and has a mesh size of 300-800.

13. A sample processing method for a trace detector, the trace detector including a sample feeding device provided with a sample feeding part, the sample processing method comprising the steps of:
    providing a sampling substrate,
    collecting a substance from a surface of an object to be tested by contacting the sampling substrate with the surface of the object, and
    transferring the substance collected by the sampling substrate to a surface of the sample feeding part of the sample feeding device.

14. The sample processing method according to claim 13, further comprising the step of:
    detecting the substance transferred to the surface of the sample feeding part.

15. The sample processing method according to claim 13, wherein the sampling substrate is a sheet-shaped substrate and is made of at least one of Dacron™, high density polyethylene fiber, terylen, and nylon.

16. The sample processing method according to claim 13, wherein the sample feeding part is a sheet-shaped substrate.

17. The sample processing method according to claim 16, wherein the sample feeding part is made of metal.

18. The sample processing method according to claim 16, wherein the sample feeding part is a film of metal.

19. The sample processing method according to claim 16, wherein the sample feeding part is a mesh of metal.

20. The sample processing method according to claim 17, wherein the metal comprises stainless steel.

21. The sample processing method according to claim 17, wherein the metal comprises one of Ni, Cr, and Pt or one of alloys of at least one of Ni, Cr, and Pt.

22. The sample processing method according to claim 18, wherein the film of metal has a thickness of about 0.01-0.10 mm.

23. The sample processing method according to claim 19, wherein the mesh of metal comprises wires having a diameter of about 0.01-0.10 mm and has a mesh size of 300-800.

24. A trace detector, comprising:
a sample feeding device provided with a sample feeding part, wherein a substance collected by a sampling substrate can be transferred to a surface of the sample feeding part so that the substance transferred to the surface of the sample feeding part can be detected.

25. The trace detector according to claim 24, wherein the sample feeding part is formed of a metal film or a metal mesh.

* * * * *